United States Patent [19]
Sargeant et al.

[11] Patent Number: 5,211,677
[45] Date of Patent: May 18, 1993

[54] METHOD AND APPARATUS FOR MEASURING THE QUANTITY OF PARTICULATE MATERIAL IN A FLUID STREAM

[75] Inventors: John P. Sargeant, Haslum; Terje Sontvedt, Gjettum; Tom Solberg, Eidanger, all of Norway

[73] Assignee: Norsk Hydro a.s., Oslo, Norway

[21] Appl. No.: 777,014

[22] Filed: Oct. 16, 1991

[30] Foreign Application Priority Data

Oct. 17, 1990 [NO] Norway ................ 904501

[51] Int. Cl.⁵ ............... G01N 15/06; G01N 27/04
[52] U.S. Cl. ........................... 73/61.71; 73/86
[58] Field of Search ............ 73/61.75, 61.71, 86

[56] References Cited

U.S. PATENT DOCUMENTS

| | | |
|---|---|---|
| T913,010 | 8/1973 | Arnold et al. . |
| 3,678,273 | 7/1972 | Lewis . |
| 3,753,257 | 8/1973 | Arnold ........................ 73/86 X |
| 3,767,916 | 10/1973 | Lewis . |
| 3,816,773 | 6/1974 | Baldwin et al. ............. 73/61.75 X |
| 3,854,323 | 12/1974 | Hearn et al. ................ 73/61.75 |
| 3,906,780 | 9/1975 | Baldwin ...................... 73/61.75 |
| 4,240,287 | 12/1980 | Mast et al. ................... 73/61.75 |
| 4,305,278 | 12/1981 | Stewart et al. . |
| 4,337,668 | 7/1982 | Zupanick ..................... 73/86 X |

FOREIGN PATENT DOCUMENTS 0317339 5/1989 European Pat. Off. .

Primary Examiner—Hezron E. Williams
Assistant Examiner—Joseph W. Roskos
Attorney, Agent, or Firm—Wenderoth, Lind & Ponack

[57] ABSTRACT

Particles in a fluid stream are detected by utilizing one or more probes each provided with at least one measuring or erosion element. The probe is placed in the fluid stream, and the particle content is quantitatively determined by measuring changes of electrical resistance as a function of erosion of the measuring element due to contact with particles moving in the stream. The probe may be equipped with a measuring head having a V-shaped configuration directed upstream, and the two planar surfaces defining the V-shape may each be equipped with one or more measuring elements.

14 Claims, 8 Drawing Sheets

RESPONSE AS A FUNCTION OF SAND RATE

— STREAM SPEED = 6 M/S, ANGLE = 55°

RESPONSE AS A FUNCTION OF STREAM SPEED

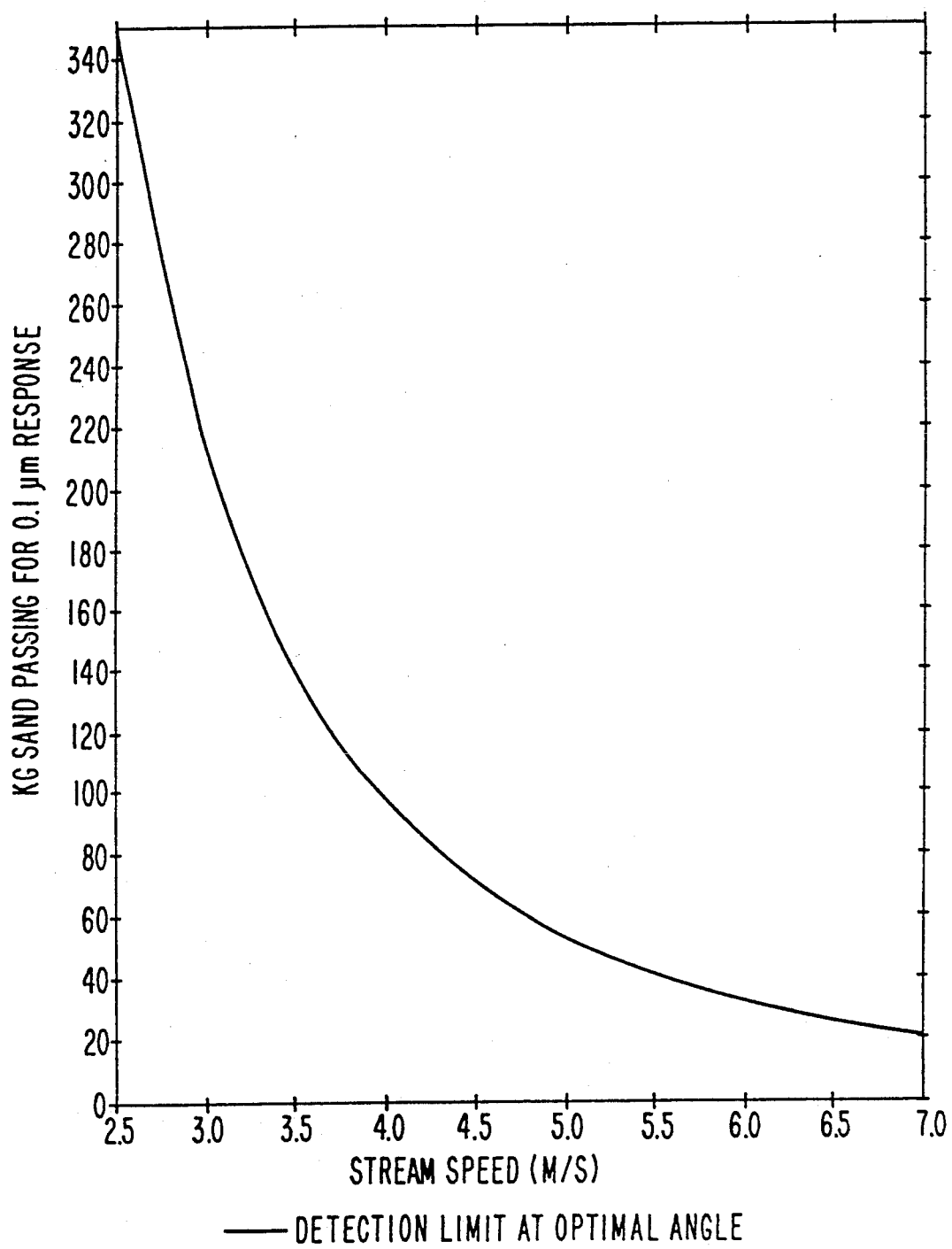

METHOD AND APPARATUS FOR MEASURING THE QUANTITY OF PARTICULATE MATERIAL IN A FLUID STREAM

BACKGROUND OF THE INVENTION

The present invention relates to a process and apparatus, including a probe, for quantitative detection of particles in a fluid stream.

Sand is often found in streams of oil and/or gas produced from underground reservoirs. The sand particles may have diameters of up to 1000 µm and may be present in quantities exceeding 25 ppm. Sand particles not only cause serious wear of production equipment, but will also potentially accumulate in the equipment, thereby causing production stoppage and serious damage. Equipment now commercially available cannot measure with sufficient accuracy the presence of sand in fluids.

The description of this invention will analyze different types of equipment which can be used or which are suggested for use in monitoring or detecting the presence of sand in fluid streams. Disadvantages of the equipment also will be described. For example, the prior art includes a probe based on the concept that sand erodes through a thin, hollow-walled body placed in a fluid stream. The difference in pressure between the fluid stream and a reference level activ an alarm when a certain value is reached, that is when a hole is formed in the hollow body. The probe then has a significant time-delay before registering the presence of sand, and the probe cannot be used for continuous monitoring. The probe is also unable to provide a quantitative measurement of sand present in the fluid stream.

Various acoustic probes also are well known. These probes are mounted either in a conduit or on its outer side. The probes can detect the presence of sand in an otherwise pure gas or liquid. Their capacity to discriminate between sand and noise attributable to other sources is, however, unsatisfactory in intermittent streams. Calibration of the units must be performed at the actual production site and must be executed by injection of sand into the production system. However, the calibration changes when the rate of production or when other sources of noise change. Also, when fine particles are produced 0–0.1 mm in diameter), their acoustic energy is too small to discriminate between particle and stream noise. An example of such probe is disclosed in Norwegian Patent No. 140838.

U.S. Pat. No. 3,678,273 discloses a procedure for measuring wear caused by an abrasive fluid. A detector coated with radioactive material is placed in a fluid stream of, for example, oil slurry containing catalytic particles. The detector is activated by radiation from the radioactive coating as it is diminished by the particulate contents of the fluid. The detector is coupled to a monitoring and measuring unit on the outside of the conduit. This patent describes detection of particles in streams of either liquid or gas, and the detector is placed in an area of anticipated uniform current. It is stated that the particulate content in the stream can be estimated. Since the detector itself is placed in the fluid stream, the detector will partially block the stream. The detector will be unable to register fine particles since these will be deflected and will follow the flow of the fluid. This detector will be unable to register fine particles since these will be deflected and will follow the flow of the fluid. This detector will not be useful for example in a high pressure hydrocarbon conduit where it is impossible to predict sand distribution. The accuracy and method of particulate content determination is not mentioned. Such method requires calibration as well as a completely uniform concentration of solids.

Norwegian Pat. Application No. 892819 (PCT/NO89/00112) describes a procedure for detection of particles in a production stream. Such method is based on the application of activated probes giving off radiation sensed by detectors placed on the outside of the stream. Each probe sends signals to one detector. The particle concentration can be determined when 0.25% of the thickness is lost. Such particular method, however, has several disadvantages. Because of dependence upon use of radioactive material, special precautions must be taken both with regard to construction of the equipment and handling of the radioactive material. This means that the equipment is complicated and expensive to build and use. Although measuring accuracy under ideal conditions is reasonably good, the external environment (background radiation, ambient temperature) can affect the measurements, and statistical uncertainty of measured data could be high.

SUMMARY OF THE INVENTION

In view of the problems of the prior art, it has been sought to provide a method of and equipment for quantitatively detecting particles in an oil and/or gas stream. wherein such equipment has a high measuring accuracy, is inexpensive, is simple to build and use, and is robust and unaffected by the external environment.

Surprisingly, it was found that it was possible to apply a method and a probe based on the principle that resistance of a measuring element (an erosion element or resistance element) placed in an oil/gas stream containing particles will change as a consequence or erosion of the measuring element by particles in the stream.

The present invention provides a solution for quantitatively measuring particles in a fluid stream without the problems of handling radioactive materials. Instrumentation is simple and robust. It is possible to arrange several measuring elements on the same probe, such that measuring accuracy can be increased and the distribution of particles in a fluid stream can be determined over an entire cross section of a conduit. This is an essential advantage with the present invention inasmuch as previously known solutions were unable to register uneven distributions of particles in a fluid stream. The inventive probe and equipment also are not affected by the external environment, and furthermore there is no statistical uncertainty in measured data. Still further, another essential advantage of the present invention is that it is unnecessary to calibrate the probe or equipment, and measuring accuracy is very high, better than the measurement procedure described in Norwegian Patent Application No. 892819, that represents the most effective solution in the prior art.

BRIEF DESCRIPTION OF THE DRAWINGS

The present invention now will be described in detail with reference to the accompanying drawings, wherein:

FIGS. 4–8 are graphs showing results derived from tests with the probe in the test rig shown in FIG. 3.

DETAILED DESCRIPTION OF THE INVENTION

As stated in the preceding description, the present invention is based on the principle that the electrical resistance of a measuring element placed in an oil/gas stream containing particles will change as the measuring element is eroded by the particles.

Figure 1A:
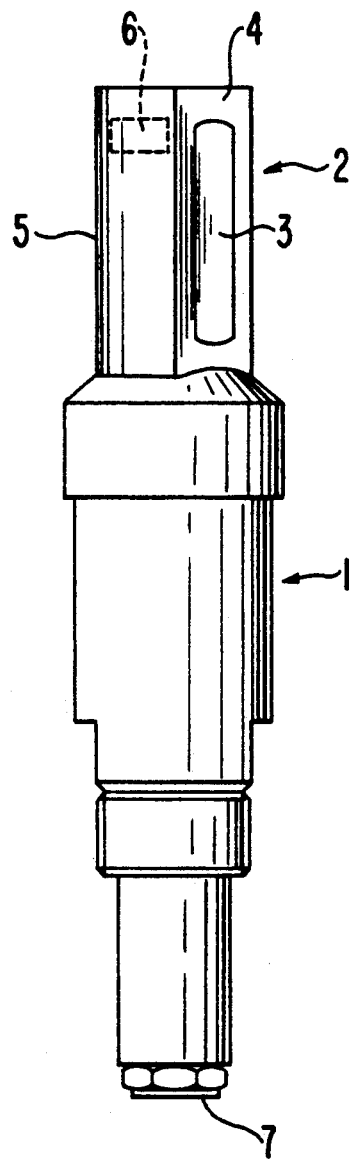
FIGS. 1a and 1b respectively are a side view and a top plan view of an embodiment of an erosion probe.
Figure 1B:
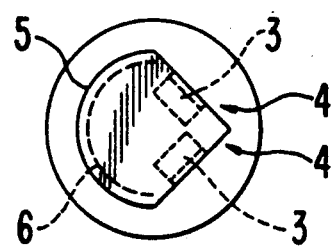

FIGS. 1a and 1b show an embodiment of an erosion probe developed to test the inventive concept. The probe consists of a body part 1 with a measuring head 2. The probe is adapted for mounting to a wall in a conduit, as discussed below with regard to FIG. 2. The measuring head 2 has, in the direction facing or against the gas/liquid stream, a plow-like or V-shaped configuration, while the remaining part 5 of the measuring head 2 (located in a downstream or rearmost part of the head 2) has a semicircular form. Measuring elements 3 are arranged on each of sides 4 of the V-shaped part of the measuring head 2. These measuring elements 3 are partially molded into the measuring head 2 such that only an outwardly facing side of each element is exposed to the ambient environment. The measuring element 3 is, in this particular embodiment, made of Monel 400 which has advantageous properties of thermal stability, electrical resistance, and wear. Monel 400 is also durable to corrosion. This is important in order to avoid situations where the measuring elements are affected by corrosion which consequently ruins or distorts measurements.

In addition to the measuring elements 3, the probe is, as shown by a dashed line in FIG. 1, provided with a third element 6 that is completely molded into the measuring head 2 (element 6 thereby being unaffected by erosion) and that thereby serves a refrence element. Since te reference element 6 is located in the very front of the probe, the element 6 simultaneously will provide good temperature compensation. The measuring head 2 is made by molding with an electrical insulation of the Belzona type. All electrical connections (in addition to the elements 3 and 6) in the measuring head are molded in the insulation.

The other parts of the probe may be made of a suitable metallic material, such as stainless steel or a similar material. The probe is also equipped with an electrical coupling 7 which is a simple manner can be connected to a complementary coupling on a conduit connected to measuring equipment (not shown).

Figure 2:
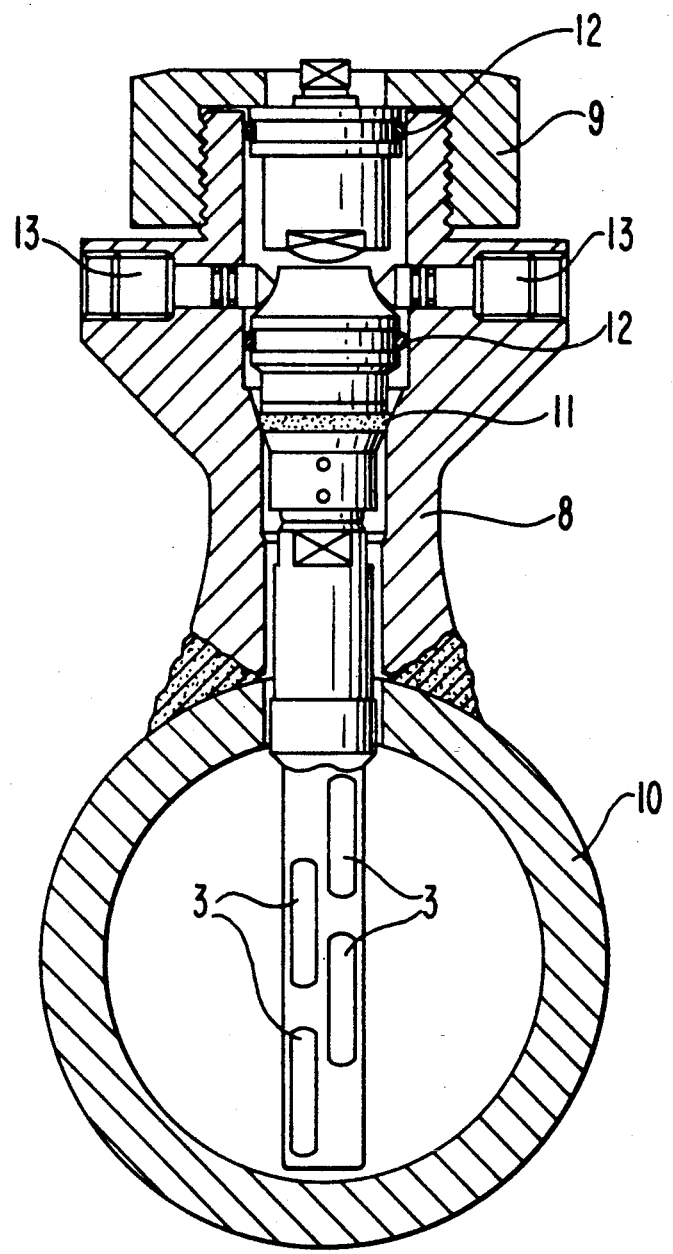
FIG. 2 is a sectional view of the probe mounted in a conduit.

FIG. 2 shows an embodiment of the inventive probe mounted in a conduit 10. As illustrated, the probe extends into the conduit 10 through a connecting piece 8 which is welded onto the conduit 10. The probe is held and secured from rotation by a hub 9 and locking screws 13. The requisite tightening between the probe and the connecting piece 8 is achieved by using gaskets 11 and 12. The probe in this embodiment is provided with four measuring elements 3, two on each of the sides of the V-shaped part of the probe. The part of the measuring head with the four elements 3 extends over the entire cross section of the conduit. As previously stated, the use of a plurality of measuring elements 3 and the extension of the probe across the entire cross section of the conduit 10 represent an important advantage of the invention, inasmuch as it is possible to determine the distribution of sand particles in a fluid stream over an entire cross section thereof by individually measuring wear of each of the elements. This has not been possible with any of the arrangements known in the prior art.

Figure 3:
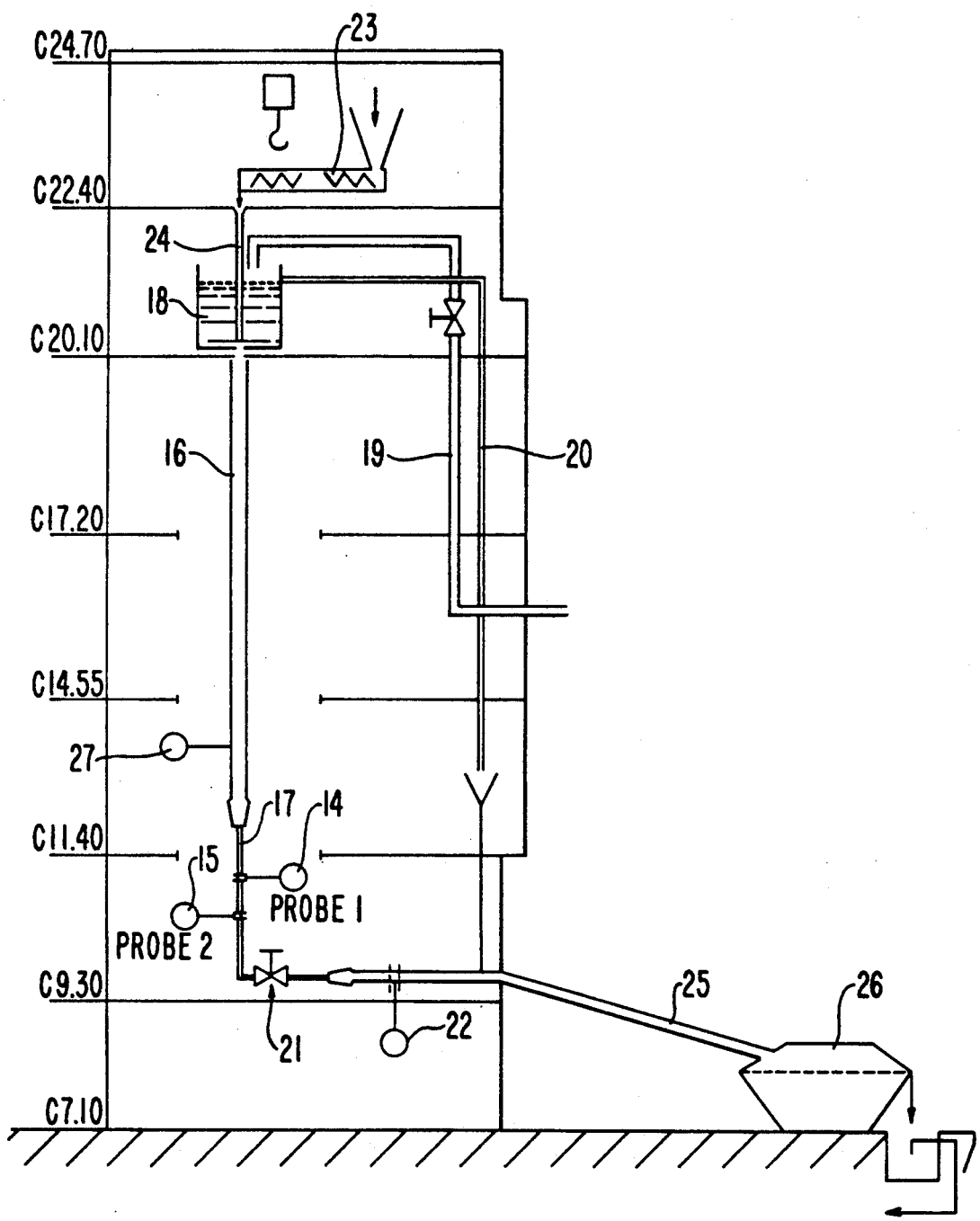
FIG. 3 is a schematic view of a test rig for the probe.

FIG. 3 shows a test rig in which the inventive probe was tested. Two test probes, an upper probe 14 and a lower probe 15, were mounted in a conduit 17 downstream of a descending conduit 16. A probe with two measuring elements as shown in FIG. 1 was used for the tests. Water was fed by cistern 18 to the descending conduit 16. Constant pressure in the descending conduit 16 was achieved by refilling the cistern 18 via a feeding line 19 with superfluous water being drained off through a spillway 20. The water flow through the testing section where the probes are mounted was adjusted by means of adjustment valve 21 downstream of the test section. An electromagnetic stream measurer 22 in run-off pipe 25 reads the water flow. Sand was added via a vibrating gutter 23 mounted above the cistern 18, and the sand was conducted through a tube 24 down through the center of descending conduit 16 in order to avoid depositing the sand in the cistern 18. The run-off pipe 25 leads to a container 26 functioning as a sand separator before the water was directed to a run-off basin. The descending conduit 16 is also equipped with a thermometer 27 for determining the temperature of the water during the tests. The sand used during the tests was first sifted through a 0.7 mm cloth filter in order to remove fractions having a greater particle size. This resulted in a median particle size of 0.5 mm for the coarsest type of sand used (baskarp sand 55).

Twelve tests were conducted to measure wear of the probes, that is reduction of the thickness of the measuring elements on the probes, as a function of time (wear was measured as a response "r" in nanometers/hour). The data from the lower probe was used to adapt the following function to the response r (nm/hour):

$$r = A \cdot S \cdot F^B \cdot \mathrm{Sin}\,(1.65\,a)^c$$

wherein A, B and C are estimated to be:
 A $= 2.911\ 10^{-12}$
 B $= 2{,}713$
 C $= 3.488$ and where
 S $=$ sand concentration in ppm (weight)
 F $=$ flowthrough in liters per minute
 $a =$ angle in degrees of element to stream flow The factor 1.65 with which $a$ is multiplied is chosen such that there is a maximum response at 60 $=55$ degrees (1.65 $\times 55 \sim 90$ degrees).

This factor may also be estimated to be value of 1.43 which given maximum response when 60 $=63$ degrees. At the same time, A, B and C are changed to
 A $= 1.304\ 10^{-12}$, B $= 2.849$ and C $= 2.44$ Overall, such two models give about equally good adjustment of data from the lower probe:
$R^2 = 97.1\%$ with 1.65 and $R^2 = 97.4$ with 1.43 This means that respectively 97.1% and 97.4% of the responses are explained by the respective models.

The function referred to above may be brought over into a more generalized form where the amount of sand (P) per period of time in a fluid stream is calculated as follows:

$$P = \frac{(Apm^{1.5})}{(Vm^B \cdot f \cdot d_p \cdot N)} \cdot \sum_{1}^{N} r$$

where
 r $=$ the response (the wear)

N = number of elements extending through the cross section
ρm = fluid mixture,s density
Vm = speed of the mixture
$d_p$ = particle size in nm
f = function which is dependent on the shape and orientation of the elements in relation to the fluid stream. For the elements described above in the given inventive embodiment, f = Sin (1.43 ×63 degrees) where the optimum angle α is 63 degrees.

The parameters A and B are estimated constants.

As stated above, twelve tests were performed to test the probes. The test program was arranged such that these twelve tests would give sufficient data to estimate the effects of the angle of the measuring elements, sand concentration and stream velocity in order to demonstrate the suitability of the present invention. The measurements show in all the tests an unambiguous and linear response.

Figure 4:
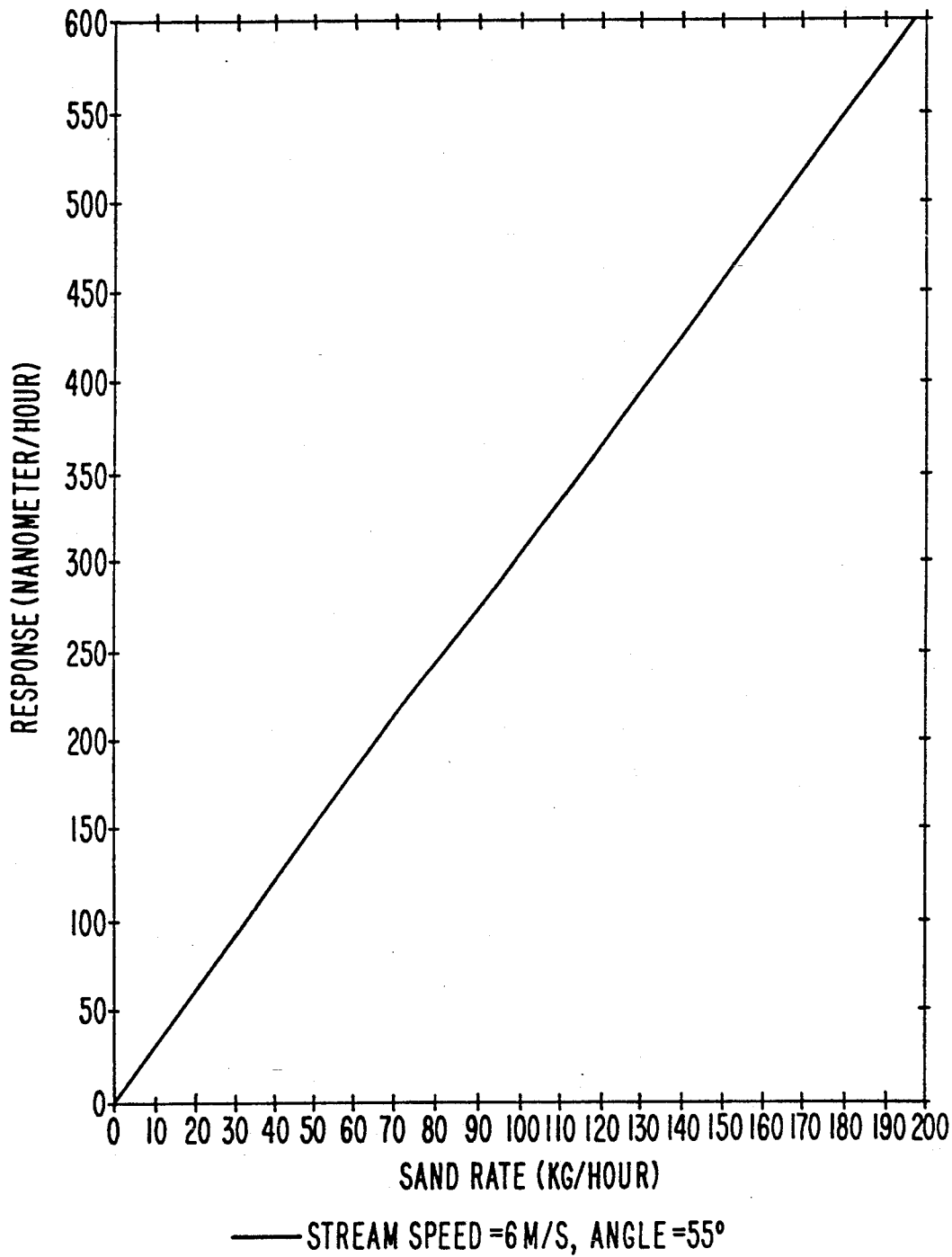

FIG. 4 shows response as a function of the rate of sand. The response in nm/hour was calculated by adjusting a line between data points in accordance with the smallest squares method. Standard deviation in the adjustments varied from 1% for the highest wear to about 10% in the cases with the lowest rate. Stability in the measurements was found to be very good with water flowthrough up to 15 hours in some tests. Variations in measurements were within +/−50nm.

Figure 5:
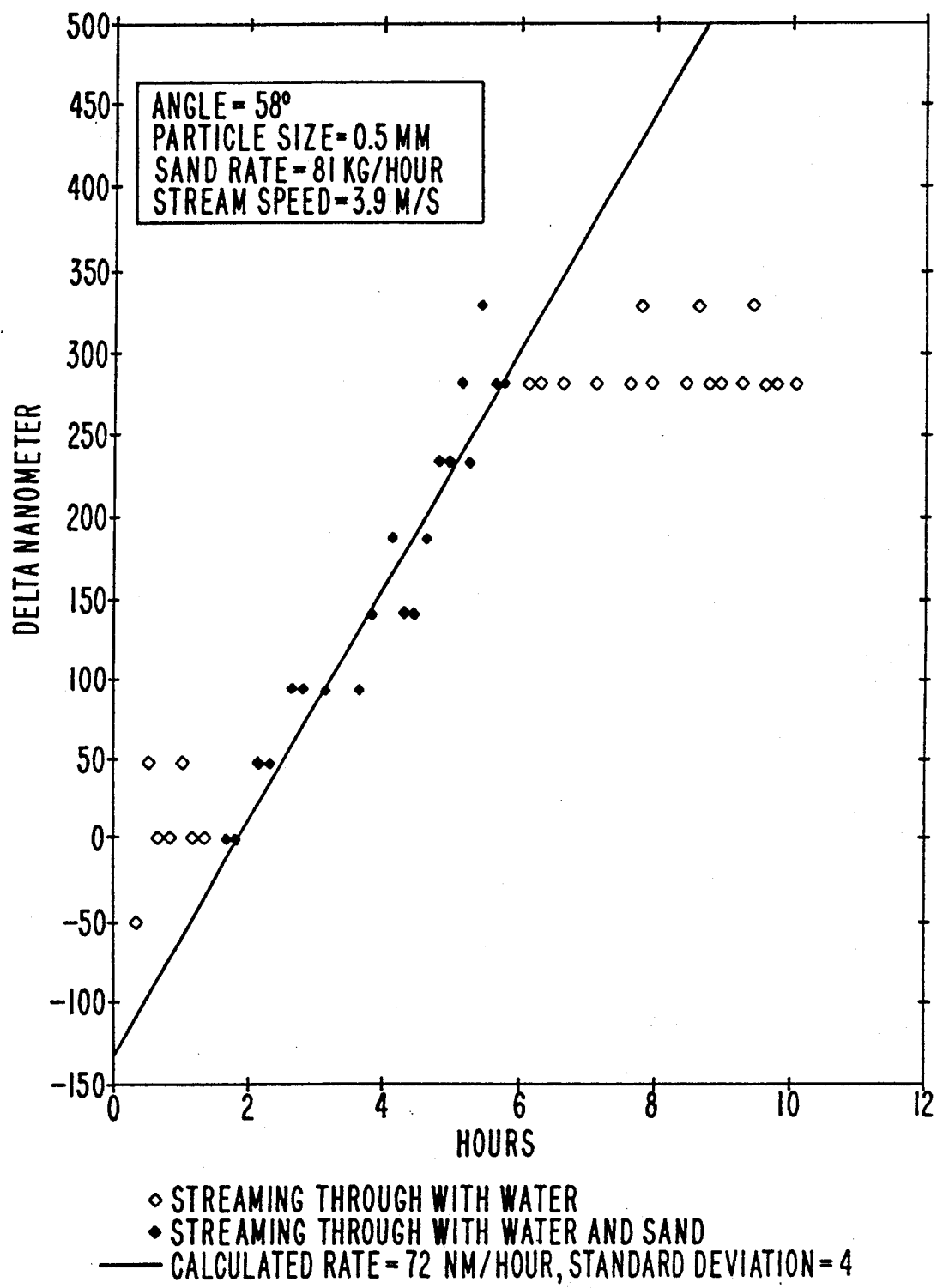

FIG. 5 shows results from one of the tests where the response r in delta nanometers (Δ nm) is shown as a function of time (in hours). The angle of the measuring element under this test was 58 degrees, the sand rate was 81 kg/hour and the flow speed was 3.9 meters per second. The erosion of the measuring elements is specified to be about 50 nm. This gives a detection limit of about 00 nm (0.1 μm) or 0.1% in the case of the measuring equipment used and with a 100 μm thick measuring element. The sensitivity is proportional to the thickness (0.1% of the thickness). This means that use of a measuring element of 10 μm will be able to increase sensitivity to 0.01 μm, but in such a case the lifetime of the element will be correspondingly reduced, that is to 1/10 of a measuring element with a 100 μm thickness. A combination of increased measuring accuracy and more frequent measurements will be able to further increase sensitivity.

Figure 6:
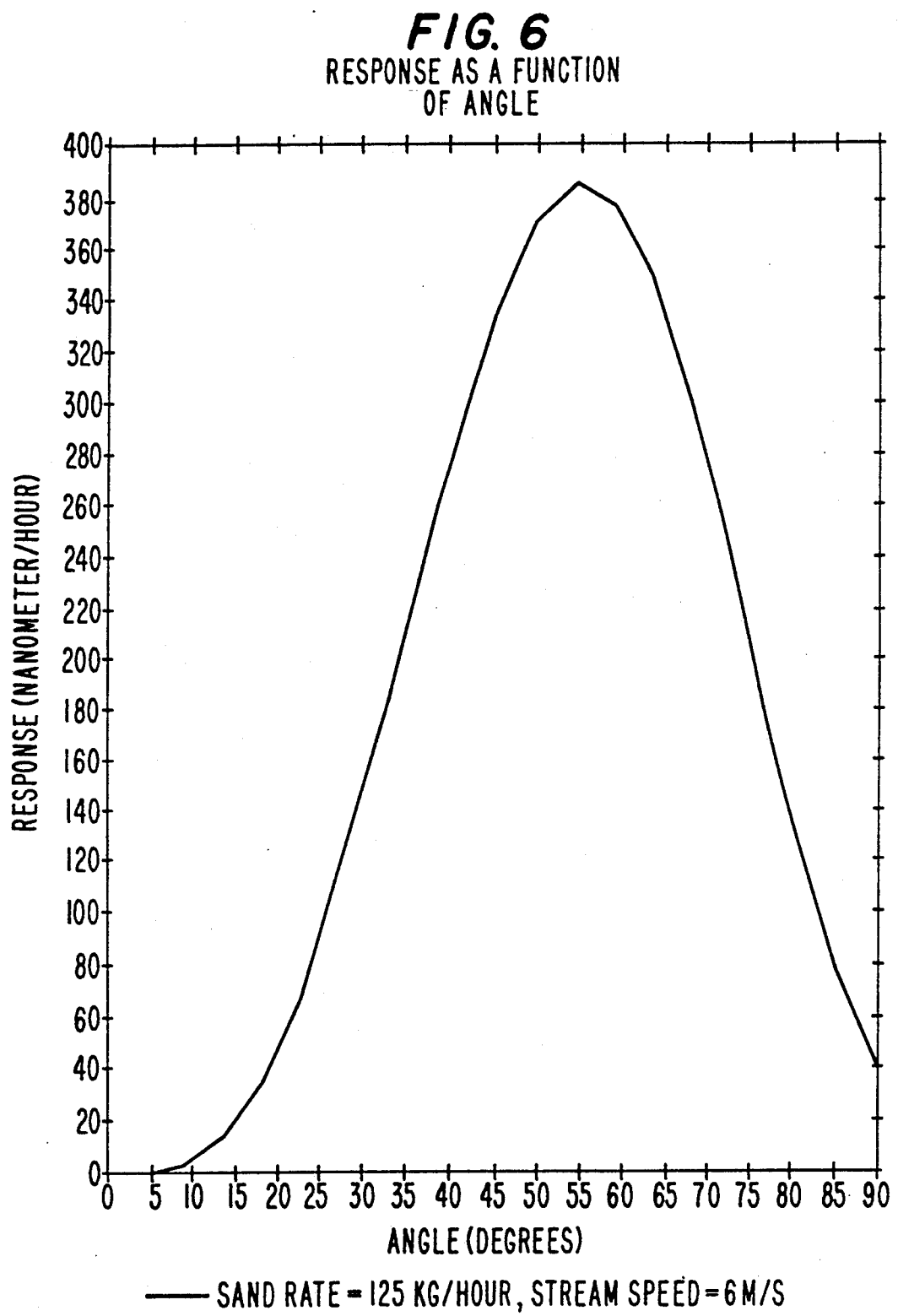

FIG. 6 shows the calculation of wear as a function of the angle of the measuring element. As shown, the sensitivity (the wear/the erosion of the measuring element) is greatest at an angle between 50 and 65 degrees. The optimum angle as previously stated is found to be at 63 degrees.

Figure 7:
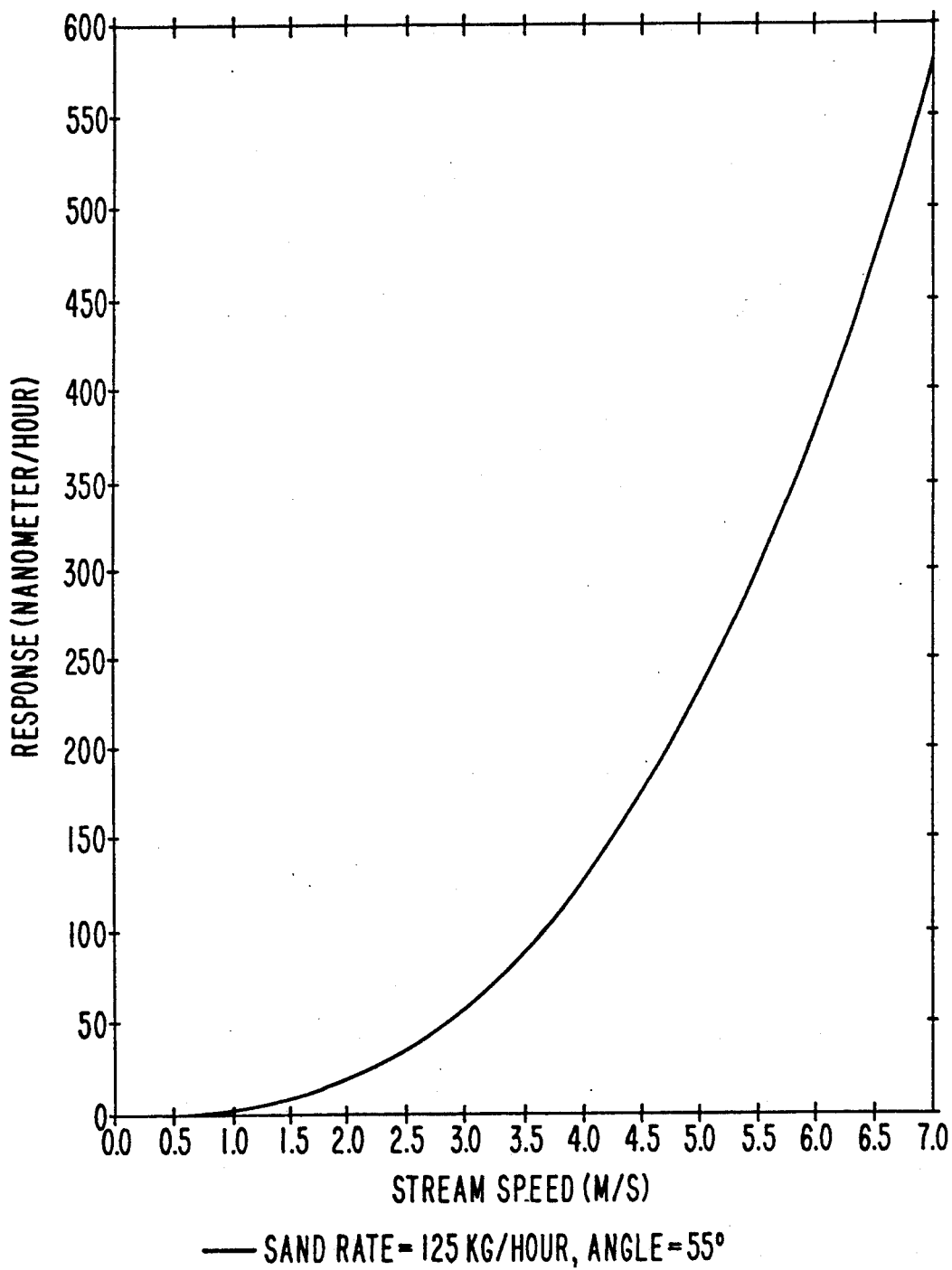

FIG. 7 shows calculated wear as a function of stream flow at a given angle of 55 degrees for the measuring element and with a sand rate of 125 kg per hour. The results show that the response is exponential in relation to the stream velocity, with an exponent of about 3.7.

FIG. 8 shows calculated sensitivity as a function of stream velocity. For each response, there was calculated minimum time for certain detection together with the amount of said (kg) passing the probe for the same deflection (0.1 μm). In the best cases, a secure detection was measured (although with the limitations referred to above) even after about 20 kg of sand had passed by the test section with a stream velocity of about 6 meters per second. This shows that the inventive probe has substantially better sensitivity than probes previously known.

Some of the tests were done with sea water. The intention was to determine if the probes were affected by a moderately conductive medium. However, it was not possible to determine any difference between the two types of water.

As stated above, tests were performed with a probe having a particularly defined shape. The probe included two measuring elements and a reference element, and has a V-shaped measuring head on which the measuring elements were arranged angularly relative to each other. It should be noted that the invention is not limited to such a construction. The probe can have a different form and be provided with several measuring elements and can for example extend completely through the cross section of the conduit. Furthermore, one or a plurality of probes can be used in connection with a measuring arrangement, and it may be advantageous to use other materials than those particularly given in the measuring elements, for example, nickel or stainless steel.

We claim:

1. A method for measuring the quantity of particulate material in a fluid stream, said method comprising:
   positioning within said fluid stream at least one measuring element that has the property of being worn errosively by said particulate material in said fluid stream and that has an electrical resistance that varies as a function of the degree of such wear;
   measuring changes of said electrical resistance of said measuring element and determining said detree of wear thereof; and
   determining the quantity (P) of said particulate material in said fluid stream according to:

$$P = \frac{(A\rho m^{1.5})}{(Vm^B \cdot f \cdot d_p \cdot N)} \cdot \sum_1^N r$$

wherein:
r = said degree of wear;
N = the number of measuring elements positioned within said stream
ρm = density of fluid mixture
Vm = speed of fluid structure
$d_p$ = particle size of particulate material
f = function that is dependent on the shape and orientation of said at least one measuring element
A and B = estimated constants.

2. A method as claimed in claim 1, comprising positioning plural said measuring elements within said fluid stream.

3. A method as claimed in claim 1, comprising providing said at least one measuring element on a probe positioned to extend across said fluid stream.

4. A method as claimed in claim 3, comprising providing plural said measuring element on said probe.

5. A method as claimed in claim 3, comprising positioning plural said probes to extend across said fluid stream, and providing at least one said measuring element on each side probe.

6. An apparatus for measuring the quantity of particulate material in a fluid stream, said apparatus comprising:
   at least one probe positionable to extend across the fluid stream; and
   said at least one probe having thereon at least one corrosion resistant measuring element that has the property of being worn errosively by the particulate material in the fluid stream, that has an electrical resistance that varies as a function of the degree of such wear, and that thereby forms means for, upon measurement of changes of electrical resistance thereof and determination of the degree of wear thereof, determining the quantity (P) of the particulate material in the fluid stream according to:

$$P = \frac{(A\rho m^{1.5})}{(Vm^B \cdot f \cdot d_p \cdot N)} \cdot \sum_{1}^{N} r$$

wherein:
r = the degree of wear
N = the number of measuring elements positioned within
ρm = density of fluid mixture
Vm = speed of fluid structure
$d_p$ = particle size of particulate material
f = function that is dependent on the shape and orientation of said at least one measuring element
A and B = estimated constants.

7. An apparatus as claimed in claim 6, comprising plural said measuring elements on said probe.

8. An apparatus as claimed in claim 6, comprising plural said probes, each said probe having thereon at least one said measuring element.

9. An apparatus as claimed in claim 8, wherein each said probe has thereon plural said measuring elements.

10. An apparatus as claimed in claim 6, wherein said probe includes a measuring head having a V-shaped configuration to be directed upstream relative to the direction of flow of the fluid stream and defined by two planar, flat surfaces each having thereon at least one said measuring element.

11. An apparatus as claimed in claim 10, wherein each said measuring element is inclined relative to the flow direction at an angle of 55° to 63°.

12. An apparatus as claimed in claim 6, wherein said measuring element is mounted to extend in a direction inclined relative to the direction of flow of the fluid stream at an angle of 55° to 63°.

13. An apparatus as claimed in claim 6, wherein said probe includes a measuring head having a circular shape having thereon plural said measuring elements configured to conform to said shape of said measuring head.

14. An apparatus as claimed in claim 6, wherein said measuring element is formed on monel.

* * * * *